United States Patent [19]

Frain et al.

[11] 3,934,991

[45] Jan. 27, 1976

[54] NITRIC OXIDE ANALYSIS AND SCRUBBER THEREFOR

[75] Inventors: John P. Frain, Costa Mesa; John N. Harman, III, Placentia; Radhakrishna M. Neti, Brea, all of Calif.

[73] Assignee: Beckman Instruments, Inc., Fullerton, Calif.

[22] Filed: Mar. 1, 1971

[21] Appl. No.: 119,601

[52] U.S. Cl. .................................. 55/316; 55/387
[51] Int. Cl.² ..................................... B01D 39/04
[58] Field of Search .. 55/68, 74, 316, 387, DIG. 30; 23/25; 252/428, 443

[56] References Cited
UNITED STATES PATENTS

| | | | |
|---|---|---|---|
| 2,825,701 | 3/1958 | Hermann et al. | 252/443 |
| 3,271,322 | 9/1966 | Stiles | 252/428 |
| 3,423,328 | 1/1969 | Keith et al. | 252/428 |
| 3,498,743 | 3/1970 | Kyllonen | 23/25 |
| 3,579,305 | 5/1971 | Neti | 23/25 |

*Primary Examiner*—Charles N. Hart
*Attorney, Agent, or Firm*—R. J. Steinmeyer; P. R. Harder

[57] ABSTRACT

A method of analyzing nitric oxide (NO) in a gas stream containing nitrogen dioxide ($NO_2$) and a scrubber apparatus for selectively removing nitrogen dioxide from a gas stream containing nitric oxide. The scrubber apparatus comprises a container having an inlet port for the gas stream and an outlet port. The scrubber material in the container includes silver carbonate whereby the scrubber has an efficiency of at least about 99% and a capacity of about 11.5 parts per million hours of 99% nitrogen dioxide removal per gram of silver carbonate. The method involves passing the gas stream through a scrubber material containing silver carbonate so as to remove nitrogen dioxide from the gas stream while passing the nitric oxide unattenuated and thereafter conveying the gas stream from the scrubber material to an analyzer for nitric oxide. The gas stream is analyzed with the analyzer to determine the nitric oxide concentration therein.

5 Claims, 1 Drawing Figure

U.S. Patent  Jan. 27, 1976  3,934,991
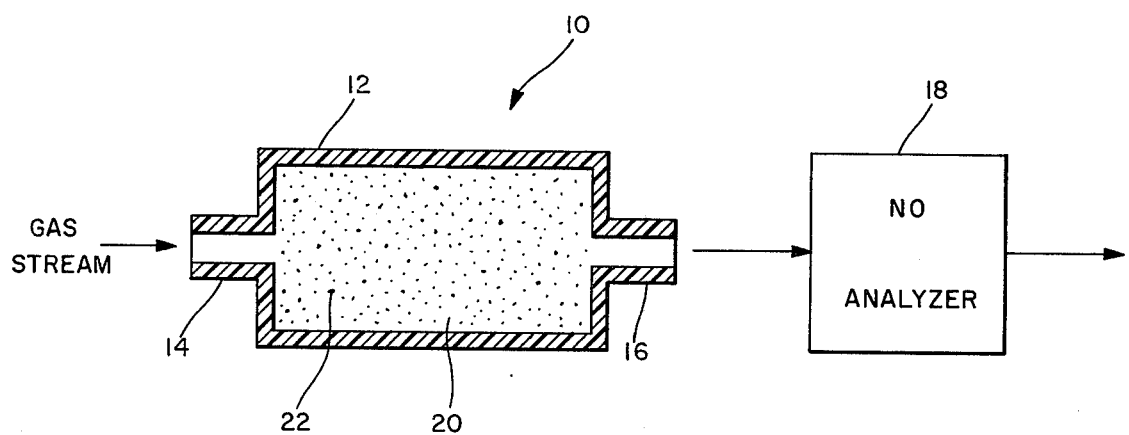

NITRIC OXIDE ANALYSIS AND SCRUBBER THEREFOR

BACKGROUND OF THE INVENTION

This invention relates to gas analysis, and more particularly, to a method or process for determining the nitric oxide content of a gas stream and also to a scrubber apparatus which is capable of selectively removing nitrogen dioxide from a gas stream without affecting the nitric oxide content thereof.

Nitric oxide is a common irritating component found in polluted air. In order that levels of this constituent may be known, means are required for practically and inexpensively determining the level of nitric oxide in air. While the description of the present invention relates particularly to the determination of nitric oxide in air, it is to be understood that the invention is applicable to the determination of nitric oxide in any gas stream which also contains nitrogen dioxide. The two gases, nitric oxide and nitrogen dioxide, are usually found together in polluted air and in other gas streams.

There are a variety of analytical instruments and analytical techniques available today for determining the content of certain irritating gaseous species in gas streams such as polluted air. One such instrument is described in U.S. Pat. No. 3,314,864 to Hersch, the description of which is incorporated by reference herein. How such an instrument is used to analyze nitric oxide is described in commonly owned U.S. Pat. 3,652,227 issued Mar. 28, 1972. Another analytical procedure and the necessary apparatus therefor is described in the U.S. Department of Health, Education and Welfare Public Health Service publication No. 999-AP-111, Selected Methods for the Measurement of Air Pollutants in a chapter entitled "Determination of Nitrogen Dioxide and Nitric Oxide: Saltzman Method" with specific reference to pages C-1 through C-7 inclusive, which is also incorporated by reference herein.

In the technique utilizing a Hersch cell, the nitric oxide is converted by reaction with ozone to form nitrogen dioxide which gives a reading in the instrument. Accordingly, one gas must be removed from the gas stream before the other can be measured. Similarly, in the Saltzman technique, the nitric oxide is first converted to nitrogen dioxide and then the amount of nitrogen dioxide determined. Here again, the original nitrogen dioxide must be removed from the stream before the nitric oxide can be determined as nitrogen dioxide.

In both cases, as is true of other analytical techniques and instruments, it is desired the nitrogen dioxide be removed substantially completely in a scrubber through which the nitric oxide will pass substantially unattenuated. Activated carbon has been tried as a scrubber material. Activated carbon does remove nitrogen dioxide but it also reduces the level of nitric oxide in the gas stream. A reduction of nitrogen dioxide to nitric oxide is observed with a ferrous sulfate scrubber material. In other words, the scrubber serves as a source of nitric oxide when it has been exposed to nitrogen dioxide. This is a significant problem for use with a nitric oxide analyzer which is to be specific for nitric oxide which is present, as is so frequently the case, in a gas stream containing both nitric oxide and nitrogen dioxide.

SUMMARY OF THE INVENTION

It is an object of the instant invention to remove nitrogen dioxide from a nitric oxide containing gas stream while passing the nitric oxide substantially unattenuated.

It is a further object of the instant invention to provide a scrubber apparatus for selectively removing nitrogen dioxide from a gas stream containing nitric oxide.

It is a further object of the instant invention to provide a method of analyzing nitric oxide in a gas stream containing nitrogen dioxide.

It is an advantage of the instant invention that it is capable of removing at least about 99% of the nitrogen dioxide from the gas stream while the concentration of nitric oxide is substantially unattenuated. It is an advantage of the instant invention that the removal of the nitrogen dioxide, unlike prior art techniques, does not result in the generation of additional nitric oxide.

According to the instant invention, a scrubber apparatus is provided for selectively removing nitrogen dioxide from a gas stream containing nitric oxide. The apparatus includes a container having an inlet port for the gas stream and an outlet port. A scrubber material is provided in the container which includes silver carbonate. The scrubber has an efficiency of at least about 99% and a capacity of about 11.5 parts per million hours of 99% nitrogen dioxide removal per gram of silver carbonate.

The silver carbonate desirably is in the form of particles having a size range of from about 1.68 millimeters to about 0.841 millimeters. If the container contains about 8.1 grams of silver carbonate, at least about 99% nitrogen dioxide may be removed for 11.5 parts per million hours per gram.

The scrubber material may be silver carbonate or a mixture of silver carbonate and other particles, e.g. polytetrafluoroethylene particles. If a mixture is used, it may contain from about 10% to about 70% by weight silver carbonate.

According to the instant invention a method is also provided for analyzing nitric oxide in a gas stream containing nitrogen dioxide. The gas stream is passed through a scrubber material containing silver carbonate so as to remove nitrogen dioxide from the gas stream while passing the nitric oxide unattenuated. The gas stream is then conveyed from the scrubber material to an analyzer for nitric oxide. The gas stream is then analyzed with the analyzer to determine the nitric oxide concentration in the gas stream.

Desirably, sufficient silver carbonate is present in the scrubber material so that the scrubber material has an efficiency of at least about 99% and a capacity of about 11.5 parts per million hours of 99% nitrogen dioxide removal per gram of silver carbonate.

The gas stream may contain up to about 8.1 parts per million nitrogen dioxide, in which case the gas stream from the scrubber material will contain not more than about 0.081 parts per million nitrogen dioxide. If the gas stream contains about 8.1 parts per million nitrogen dioxide and the scrubber material contains about 8.1 grams silver carbonate, the gas stream from the scrubber material will contain less than about 0.081 parts per million nitrogen dioxide for about 11.5 hours. The nitric oxide concentration of the gas stream desirably may range from about 0.07 parts per million to about 2.4 parts per million (ppm).

Other objects and advantages of the instant invention will become apparent from the following detailed description taken in conjunction with the accompanying drawing.

BRIEF DESCRIPTION OF THE DRAWING

The drawing is a schematic view in section of apparatus useful is the practice of the instant invention.

DETAILED DESCRIPTION

Referring now to the single figure of the drawing, there is shown a scrubber apparatus generally designated 10 which preferably comprises a container 12 of suitable material, e.g. glass or plastic. Container 12 has an inlet 14 adapted to receive the gas stream and an outlet 16 which may be, for example, connected in a suitable manner, not shown, to a nitric oxide analyzer 18.

The nitric oxide analyzer may, for example, be a galvanic cell of the type disclosed in the aforementioned Hersch patent and attendant ozone apparatus or may be a colorimetric instrument and attendant conversion apparatus for determining nitric oxide in accordance with the Saltzman method discussed in the U.S. Public Health Service publication No. 999-AP-ll mentioned above.

The gas stream being analyzed is introduced into scrubber 10 via inlet port 14 and will pass through chamber 20 thereof and exit through outlet 16 into the nitric oxide analyzer 18.

Compartment 20 of scrubber apparatus 10 is filled with scrubber material 22. Scrubber material 22 includes silver carbonate. The silver carbonate may be provided in bulk granular form, for example, in the form of particles having a size range from about 1.68 millimeters to about 0.841 millimeters (10 to 20 mesh). It may also be mixed with a suitable powdered dispersing agent such as polytetrafluoroethylene. The particle size range of the polytetrafluoroethylene does not seem to be of significance. Particle size ranges from about 0.235 millimeters to about 0.354 millimeters and particles of a size about 0.500 ±0.15 millimeters have been used with no noticeable difference in results.

The silver carbonate appears to function by an adsorption process for the removal of nitrogen dioxide with an efficiency for nitrogen dioxide removal in excess of 99% when tested at the 8 parts per million nitrogen dioxide level and a capacity of about 11.5 parts per million hours per gram. There exists little attenuation in the level of nitric oxide wheen passed through the scrubber.

The effectiveness of silver carbonate for nitrogen dioxide removal can be appreciated by considering the following example.

EXAMPLE NO. 1

A nitrogen dioxide permeation tube whose output was determined to be 8.1 parts per million nitrogen dioxide by the conventional Saltzman technique for nitrogen dioxide analysis (described in the Public Health Service publication No. 999-AP-11 incorporated by reference herein) was passed through a selective scrubber apparatus consisting of a glass tube packed with 8.1 grams of reagent grade J. T. Baker Company silver carbonate. A Beckman Model 910 Analyzer, which is an apparatus similar to that described in the above-mentioned U.S. Pats. 3,314,864 and 3,652,227 was used to detect the nitrogen dioxide concentration of the sample initially containing 8.1 parts per million nitrogen dioxide. The concentration of nitrogen dioxide in the gas stream from the scrubber was less than 0.081 parts per million for a time period of 11.5 hours. This indicates the scrubber had a scrubbing efficiency of better than 99% for nitrogen dioxide and a capacity of roughly 11.5 parts per million hours of at least 99% nitrogen dioxide removal per gram of silver carbonate.

The ability of the silver carbonate scrubber of the present invention to quantitatively transmit nitric oxide therethrough is illustrated by the following example:

EXAMPLE NO. 2

A diluted sample of nitric oxide in nitrogen (10 parts per million NO) was further diluted with nitrogen, or in some runs air, to yield various nitric oxide test gas concentrations. The concentrations prepared were approximately 2.4, 0.1, and 0.07 parts per million nitric oxide. The concentrations were determined by the Saltzman technique and by using a Beckman Model 910 Analyzer with no selective scrubber. These concentrations were in agreement(within experimental error) between the two analytical techniques. Scrubber materials containing 5 grams of silver carbonate or mechanical mixtures of silver carbonate and polytetrafluoroethylene powder were tested on these various nitric oxide test gas concentrations. The gas stream from the scrubbers were analyzed and no apparent attenuation of the sample gas stream injected into the inlet port of the scrubber was found. No difference in the test was observed using straight silver carbonate powder or a mechanical mixture of powdered silver carbonate and powdered polytetrafluoroethylene with the concentration of silver carbonate therein varying from about 70 weight percent to about 10 weight percent. In summation, these tests indicated the silver carbonate would transmit quantitatively nitric oxide in concentrations from about 0.07 to 2.5 parts per million. Higher concentrations of nitric oxide were not evaluated although there is no reason to think they would not also be quantitatively transmitted. The particle size range of the silver carbonate was the same as that described in Example 1 and two different sources of polytetrafluoroethylene powder were used. The polytetrafluoroethylene powder from one source ranged in particle size from about 0.250 millimeters to about 0.354 millimeters. The powder from the other source had a particle size of 0.500 ± 0.15 millimeters. The particle size seemed to have no effect upon the results.

It will be appreciated the foregoing is only a description of one process and one form of apparatus embodying the principles of the instant invention. This is for illustrative purposes and the instant invention is not to be limited thereby, but only by the claims wherein.

What is claimed is:

1. A scrubber apparatus for selectively removing nitrogen dioxide from a gas stream containing nitric oxide without affecting the nitric oxide content of the stream, said apparatus comprising:
   a. a container having an inlet port for the gas stream and an outlet port; and
   b. a scrubber material in the container including silver carbonate whereby the scrubber has an efficiency of at least about 99% and a capacity of about 11.5 ppm hours of 99% nitrogen dioxide removal per gram of silver carbonate.

2. The scrubber apparatus of claim 1 wherein the silver carbonate is in the form of particles having a size range of from about 1.68 millimeters to about 0.841 millimeters.

3. The scrubber apparatus of claim 1 wherein the container contains about 8.1 grams of silver carbonate, whereby at least about 99% nitrogen dioxide may be removed for 11.5 ppm hours per gram.

4. The scrubber apparatus of claim 1 wherein the scrubber material is a mixture of silver carbonate and polytetrafluoroethylene particles.

5. The scrubber apparatus of claim 4 wherein the mixture contains from about 10% to about 70% by weight silver carbonate.

* * * * *